(12) United States Patent
Lelie et al.

(10) Patent No.: US 11,547,353 B2
(45) Date of Patent: *Jan. 10, 2023

(54) IMPLANT EVALUATION USING ACOUSTIC EMISSIONS

(71) Applicant: BBI Medical Innovations, LLC, Los Angeles, CA (US)

(72) Inventors: Herman Louis Lelie, Los Angeles, CA (US); Graham Oliver Ross, Oceanside, CA (US); Pauldeep Singh Mann, Fowler, CA (US)

(73) Assignee: BBI Medical innovations, LLC, Los Angeles, CA (US)

( * ) Notice: Subject to any disclaimer, the term of this patent is extended or adjusted under 35 U.S.C. 154(b) by 162 days.

This patent is subject to a terminal disclaimer.

(21) Appl. No.: 17/130,287

(22) Filed: Dec. 22, 2020

(65) Prior Publication Data

US 2021/0106277 A1    Apr. 15, 2021

Related U.S. Application Data

(63) Continuation of application No. 16/206,604, filed on Nov. 30, 2018, now Pat. No. 10,918,333.

(Continued)

(51) Int. Cl.
*A61B 8/00* (2006.01)
*G01N 29/14* (2006.01)
(Continued)

(52) U.S. Cl.
CPC .......... *A61B 5/4851* (2013.01); *A61B 5/4504* (2013.01); *A61B 5/4528* (2013.01);
(Continued)

(58) Field of Classification Search
CPC ....... A61B 5/00; A61B 5/1036; A61B 5/5404; A61B 5/4528; A61B 5/4851;
(Continued)

(56) References Cited

U.S. PATENT DOCUMENTS

| 4,819,753 A | 4/1989 | Higo et al. |
| 5,024,239 A | 6/1991 | Rosenstein |

(Continued)

FOREIGN PATENT DOCUMENTS

| EP | 3220373 A1 | 9/2017 |
| EP | 3551137 | 10/2019 |

(Continued)

OTHER PUBLICATIONS

Agcaoglu et al., "Acoustic Emission Based Monitoring of the Microdamage Evolution During Fatigue of Human Cortical Bone," ASME. *J Biomech Eng.* 2013;135(8):081005.

(Continued)

*Primary Examiner* — Nguyen Q. Ha
(74) *Attorney, Agent, or Firm* — Arnold & Porter Kaye Scholer LLP

(57) ABSTRACT

The present disclosure provides methods of identifying a loosened joint implant by analyzing acoustic emissions from the implant. The present disclosure further provides apparatuses for measuring acoustic data and analyzing acoustic emissions from a joint implant.

14 Claims, 6 Drawing Sheets

Related U.S. Application Data

(60) Provisional application No. 62/593,210, filed on Nov. 30, 2017.

(51) Int. Cl.
*A61B 5/00* (2006.01)
*G01N 29/44* (2006.01)
*G01N 29/42* (2006.01)
*G01N 29/48* (2006.01)
*A61B 5/103* (2006.01)

(52) U.S. Cl.
CPC ............ *G01N 29/14* (2013.01); *G01N 29/42* (2013.01); *G01N 29/4436* (2013.01); *G01N 29/48* (2013.01); *A61B 5/1036* (2013.01); *A61B 5/6812* (2013.01); *G01N 2291/011* (2013.01); *G01N 2291/02466* (2013.01)

(58) Field of Classification Search
CPC . A61B 5/6812; A61B 8/00; A61F 2/30; A61F 2/38; G01N 29/00; G01N 29/04–52; G01N 29/4436; G01N 2291/011; G01N 2291/02466
See application file for complete search history.

(56) References Cited

U.S. PATENT DOCUMENTS

| | | | |
|---|---|---|---|
| 5,170,666 | A | 12/1992 | Larsen |
| 5,533,519 | A | 7/1996 | Radke et al. |
| 5,819,007 | A | 10/1998 | Elghazzawi |
| 6,213,958 | B1 | 4/2001 | Winder |
| 6,386,038 | B1 | 5/2002 | Lewis, III et al. |
| 6,594,382 | B1 | 7/2003 | Woodall |
| 2003/0091203 | A1 | 5/2003 | Croft, III et al. |
| 2006/0047283 | A1 | 3/2006 | Evans et al. |
| 2007/0088194 | A1 | 4/2007 | Tahar et al. |
| 2007/0089518 | A1 | 4/2007 | Ericson et al. |
| 2007/0118054 | A1 | 5/2007 | Pinhas et al. |
| 2007/0265533 | A1 | 11/2007 | Tran |
| 2007/0273504 | A1 | 11/2007 | Tran |
| 2007/0276270 | A1 | 11/2007 | Tran |
| 2008/0001735 | A1 | 1/2008 | Tran |
| 2008/0262347 | A1 | 10/2008 | Batchelder et al. |
| 2010/0298650 | A1 | 11/2010 | Moon et al. |
| 2010/0305481 | A1 | 12/2010 | Igney et al. |
| 2012/0029345 | A1 | 2/2012 | Mahfouz et al. |
| 2012/0245481 | A1 | 9/2012 | Blanco et al. |
| 2012/0203491 | A1 | 11/2012 | Hill et al. |
| 2013/0021259 | A1 | 1/2013 | Sudo et al. |
| 2013/0041289 | A1 | 2/2013 | Sena et al. |
| 2013/0095459 | A1 | 4/2013 | Tran |
| 2013/0172691 | A1 | 7/2013 | Tran |
| 2013/0211259 | A1 | 8/2013 | Komistek et al. |
| 2013/0226020 | A1 | 8/2013 | Holley et al. |
| 2015/0045699 | A1 | 2/2015 | Mokaya et al. |
| 2015/0190091 | A1 | 7/2015 | Ser et al. |
| 2016/0015319 | A1 | 1/2016 | Billi et al. |
| 2016/0192878 | A1 | 7/2016 | Hunter |
| 2016/0287122 | A1 | 10/2016 | Heneghan |
| 2016/0302721 | A1 | 10/2016 | Wiedenhoefer et al. |
| 2017/0234837 | A1 | 8/2017 | Hall et al. |
| 2017/0296118 | A1* | 10/2017 | Swanson ............... A61B 5/7282 |
| 2018/0177456 | A1* | 6/2018 | Swanson ............... A61B 5/4851 |
| 2018/0289324 | A1 | 10/2018 | Kianifar et al. |
| 2019/0159724 | A1 | 5/2019 | Lelie et al. |
| 2020/0315530 | A1 | 10/2020 | Billi et al. |

FOREIGN PATENT DOCUMENTS

| | | |
|---|---|---|
| GB | 2571888 | 9/2019 |
| JP | 2010-051416 | 3/2010 |
| KR | 10-2008-0057352 | 6/2008 |
| WO | WO-0028925 A2 * | 5/2000 ......... A61F 2/30771 |
| WO | 2014/138435 | 9/2014 |
| WO | 2019/108966 | 6/2019 |

OTHER PUBLICATIONS

Akkus, "Comments on Acoustic Emission Visualization of Bone Cement Fatigue Locations," *Journal of Biomedical Materials Research*, 59:398-401 (2002).

Altman et al., "The American College of Rheumatology Criteria for the Classification and Reporting of Osteoarthritis of the Hand," *Arthritis & Rheumatism*, 33(11):1601-10 (1990).

Altman et al., "The American College of Rheumatology Criteria for the Classification and Reporting of Osteoarthritis of the Hip," *Arthritis & Rheumatism*, 34(5):505-514 (1991).

Andersson et al., The Burden of Musculoskeletal Diseases in the United States: Prevalence, Societal and Economic Cost, 2nd Ed., 75-102 (2011).

Andersson et al., *The Burden of Musculoskeletal Diseases in the United States: Prevalence*, Societal and Economic Cost, 2nd Ed., 103-27 (2011).

Andersson et al., *The Burden of Musculoskeletal Diseases in the United States: Prevalence, Societal and Economic Cost*, 2nd Ed., 219-52 (2011).

Austin et al., "Knee Failure Mechanisms After Total Knee Arthroplasty," *Techniques in Knee Surgery*, 3(1):55-9 (2004).

Baum et al., "Measuring Dynamic Knee Motion with an Instrumented Spatial Linkage Device." Gait and Clinical Movement Analysis Society, Eighth Annual Meeting, Wilmington, Delaware, USA, pp. 15-16 (2003).

Berman, "Hyaluronic Acid, Meniscal Debridement Deemed Worthless in Reviews," *Rheumatology Network* <http://www.rheumatologynetwork.com> (Sep. 2, 2014).

Bessette et al., "Total hip arthroplasty in patients younger than 21 years: a minimum 10-year follow-up," *Can J Surg*, 46(4):257-62 (2003).

Bowdler "Prototype Device to Spot Knee Osteoarthritis Unveiled," BBC News, 2 pp. (2010), http://www.bbc.com/news/health-10630883, accessed Mar. 4, 2013.

British Association for Surgery of the Knee, "Knee Replacement: A Guide to Good Practice," <http://www.boa.ac.uk/publications/tkr_good_practice/> (1999).

Browne et al., "The acoustic emission technique in orthopaedics—a review," *J. Strain Analysis*, 40(1):59-79 (2005).

Cai et al., "Knee Joint Vibration Signal Analysis with Matching Pursuit Decomposition and Dynamic Weighted Classifier Fusion," *Computational and Mathematical Methods in Medicine*, vol. 2013: Article ID 904267, 11 pages (2013).

Chen, "Discovery of acoustic emission based biomarker for quantitative assessment of knee joint ageing and degeneration," (Aug. 2011) (unpublished Ph.D. thesis, University of Central Lancashire) (on file with the Electronic Theses Online System).

Chu et al., "Acoustical Pattern Recognition of Knee Joint Diseases," *The Journal of the Acoustical Society of America*, 52(1A): 179 (1972).

Chu et al., "Detection of Knee Joint Diseases Using Acoustical Pattern Recognition Technique," *J. Biomechanics*, 9(3):111-14 (1976).

Chu et al., "Possible Clinical Application of a Noninvasive Monitoring Technique of Cartilage Damage in Pathological Knee Joints," *Journal of Clinical Engineering*, 3(1):19-27 (1978).

Cram et al., "Total Knee Arthroplasty Volume. Utilization, and Outcomes Among Medicare Beneficiaries, 1991-2010," *JAMA*, 308(12):1227-36 (2012).

Davidson et al., "Human Research Program (HRP) Overview" <https://www.nasa.gov/sites/default/files/files/RS_HRP_July2013_508.pdf> (Jul. 31, 2013).

Davies et al., "Monitoring the Integrity of the Cement-Metal Interface of Total Joint Components in vitro Using Acoustic Emission and Ultrasound," *The Journal of Arthroplasty*, 11(5):594-601 (1996).

(56) References Cited

OTHER PUBLICATIONS

Deng et al., "Study on Recognition Characteristics of Acoustic Emission Based on Fractal Dimension," *The 2008 International Conference on Embedded Software and Systems Symposia*, 475-78 (2008).

Department of Veterans Affairs, Facts about the Department of Veterans Affairs (Jan. 2009) <http://www.va.gov>.

Enad et al., "Orthopedic Injuries in U.S. Casualties Treated on a Hospital Ship during Operation Iraqi Freedom," *Military Medicine*, 173:1008-13 (2008).

Engesaeter et al., Rapport, Nasjonalt Kompetensesenter for Leddproteser ISBN 978-82-91847-15-3 Bergen, Norway (2010).

Extended European Search Report dated Jul. 27, 2020, in European Application 18883630.8.

Fan et al., "Modelling acoustic emissions generated by sliding friction," *Wear*, 268:811-815 (2010).

Frank et al., "Analysis of Knee Joint Sound Signals for Non-invasive Diagnosis of Cartilage Pathology," *IEEE Engineering in Medicine and Biology Magazine*, 9(1):65-8 (1990).

Franke et al., "Acoustic Emission Measurement System for the Orthopedical Diagnostics of the Human Femur and Knee Joint," *DGZfP-Proceedings BB 90-CD*, (2004) <http://www.ndt.net/article/ewgae2004/html/htmltxt/101schwalbe.htm>.

Fu et al., "Energy-efficient deployment strategies in structural health monitoring using wireless sensor networks," *Structural Control and Health Monitoring*, 00:1-14 (2012).

Gaber et al., "Mining Data Streams: A Review," *SIGMOD Record*, 34(2):18-26 (2005).

Glaser et al., "A non-invasive acoustic and vibration analysis technique for evaluation of hip joint conditions," *Journal of Biomechanics*, 43:426-432 (2010).

Gonzalez et al., "A Piezoelectric Plethysmograph Sensor Based on a Pt Wire Implanted Lead Lanthanum Zirconate Titanate Bulk Ceramic," *Sensors*, 10(8):7146-7156 (2010).

Grosse et al., "Improvements of AE technique using wavelet algorithms, coherence functions and automatic data analysis," *Construction and Building Materials*, 18(3):203-13 (2004).

Grosse et al., "Initial development of wireless acoustic emission sensor Motes for civil infrastructure state monitoring," *Smart Structures and Systems*, 6(3):197-209 (2010).

Gueiral et al., "Acoustic Emission Studies in Hip Arthroplasty—Peak Stress Impact In Vitro Cemented Prothesis," *Recent Advances in Arthroplasty*, pp. 131-147 (2012).

Hase et al., "Correlation Between Features of Acoustic Emission Signals and Mechanical Wear Mechanisms," *Wear* 292-293, pp. 144-150 (2012).

Heinzelman et al., "Energy-Efficient Communication Protocol for Wireless Microsensor Networks," *Proceedings of the 33rd Hawaii International Conference on System Sciences*, 1-10 (2000).

Hollis, "Non-invasive Acoustic Emission Testing of Compressed Trabecular Bone and Porous Ceramics using Seismic Analysis Techniques" (Aug. 30, 2004) (unpublished M.S. thesis, Georgia Institute of Technology) (on file with the Georgia Tech Library).

Hymes et al., "Mechanisms of Failure of Locked Plate Fixation of the Proximal Humerus: Acoustic Emissions as a Novel Assessment Modality," *Journal of Orthopaedic Trauma*, 27(7):392-8 (2013).

Integrated Healthcare Association, "Orthopedics Data Compendium: Use, Cost, and Market Structure for Total Joint Replacement" <http://www.iha.org/pdfs_documents/medical_device/07_OrthopedicsDataCompendium.pdf> (2006).

International Search Report dated Jun. 27, 2014, in International Application No. PCT/US2014/021305.

International Search Report dated Feb. 8, 2019, in International Application No. PCT/US2018/063361.

Jones et al., "An objective tool for assessing the outcome of total knee replacement surgery," *Proceedings of the Institution of Mechanical Engineers, Part H: Journal of Engineering in Medicine*, 222:647-55 (2008).

Kernohan et al., "Non-invasive Diagnosis and Prophylaxis in Orthopaedics," *Proceedings of the Institution of Mechanical Engineer*, 205:173-87 (1991).

Khan-Edmundson et al., "Tissue Attenuation Characteristics of Acoustic Emission Signals for Wear and Degredation of Total Hip Arthroplasty Implants," *8th IFAC Symposium on Biological and Medical Systems*, Biological and Medical Systems, 8(1):355-60 (2012).

Kholgi et al., "An Analytical Framework For Data Stream Mining Techniques Based On Challenges And Requirements," *International Journal of Engineering Science and Technology*, 3(3):2507-13 (2011).

Kim et al., "Classification of Joint Pathology using an Acoustical Analysis of Knee Joint Sound," *IEEE Biomedical Circuits and Systems Conference*, 65-68 (2006).

Kim et al., "An enhanced algorithm for knee joint sound classification using feature extraction based on time-frequency analysis," *Computer Methods and Programs in Biomedicine*, 94:198-206 (2009).

Kummer et al., "Feasibility of Using Ultrasonic Emission for Clinical Evaluation of Prosthetic Hips," *Bulletin of the NYU Hospital for Joint Diseases*, 68(4):262-265 (2010).

Lee et al., "Analysis of Vibroarthrographic Signals for Knee Osteoarthritis Diagnosis," *2012 Sixth International Conference on Genetic and Evolutionary Computing (ICGEC)*, pp. 223-228 (2012).

Lelis et al., "Ultrasonic Attenuation Coefficient of a Hip Prosthesis with Inclusions," *International Journal of Material and Mechanical Engineerin*, 1(6):103-7 (2012).

Li, "A brief review: acoustic emission method for tool wear monitoring during turning," *International Journal of Machine Tools & Manufacture*, 42:157-65 (2002).

Li et al., "Improving Source Location Accuracy of Acoustic Emission in Complicated Structures," *J Nondestruct Eval*, 28:1-8 (2009).

Lucas, "Nursing management issues in hip and knee replacement surgery," *British Journal of Nursing*, 13(13):782-787 (2004).

Maheshwari et al., "Multimodal Pain Management after Total Hip and Knee Arthroplasty at the Ranawat Orthopaedic Center," *Clinical Orthopaedics and Related Research*, 467(6):1418-23 (2009).

Mascaro et al., "Exploratory study of a non-invasive method based on acoustic emission for assessing the dynamic integrity of knee joints," *Medical Engineering & Physics*, 31:1013-1022 (2009).

Mavrogordato et al., "Real time monitoring of progressive damage during loading of a simplified total hip stem construct using embedded acoustic emission sensors," *Medical Engineering & Physics*, 33:395-406 (2011).

Mba, "Acoustic Emissions and monitoring bearing health." *Tribology Transactions* 46(3):447-51 (2003).

McCoy et al., "Vibration Arthrography as a Diagnostic Aid in Diseases of the Knee," *Journal of Bone and Joint Surgery*, 62-B(2):288-93 (1987).

Mollan et al., "A Critical Appraisal of Auscultation of Human Joints," *Clinical Orthopaedics & Related Research*, 170:231-37 (1982).

Nawab et al., "Functional Activity Monitoring From Wearable Sensor Data," *Proceedings of the 26th Annual International Conference of the IEEE Engineering in Medicine and Biology Society*, 979-82 (2004).

Nunez, "Acoustic Emission Wireless Sensors," <http://www.mistrasgroup.com/> (2009).

Nunley et al., "The Learning Curve for Adopting Hip Resurfacing Among Hip Specialists," *Clinical Orthopaedics and Related Research* (Published online: Sep. 25, 2009).

Olivier et al., "Diagnostic accuracy and interobserver variability of plain radiography, subtraction arthrography, nuclear arthrography, and bone scintigraphy in the assessment of aseptic femoral component loosening," *Arch Orthop Trauma Surg*, 126:316-323 (2006).

Ono et al., "Imaging Of Acoustic Emission From Vibrating Micro/Nano Structures," *19th IEEE International Conference Micro Electro Mechanical Systems*, 242-45 (2006).

Pandian et al., "Wireless Sensor Network for Wearable Physiological Monitoring," *Journal of Networks*, 3(5):21-29 (2008).

(56) References Cited

OTHER PUBLICATIONS

Paxton et al., "The Kaiser Permanente Implant Registries: Effect on Patient Safety, Quality Improvement, Cost Effectiveness, and Research Opportumties," *The Permanente Journal*, 16(2):36-44 (2012).

Paxton et al., "Evaluation of total hip arthroplasty devices using a total joint replacement registry," *Pharmacoepidemiology And Drug Safety*, 21(S2):53-9 (2012).

Paxton, "Kaiser Permanente Impalnt Registries: Enhancing Patient Safety and Quality of Care" (Aug. 26, 2013).

Peace, "Joint Replacement Infection,"(Accessed on Sep. 3, 2013) <orthoinfo.aaos.org/topic.cfm?topic=A00629>.

Piedade et al., "Revision after early aseptic failures in primary total knee arthroplasty," *Knee Surg Sports Traumatol Arthrosc*, 17:248-53 (2009).

Pomponi et al., "Real-time Acoustic Emission Classification: New Evolutionary Approach," 30th European Conference on Acoustic Emission Testing & 7th International Conference on Acoustic Emission, University of Granada (2012).

Prior et al., "The Joint Acoustic Analysis System (JAAS) for Assessment and Monitoring of Arthritis in Knees," *Rheumatology*, 47 (suppl 2): ii178-80 (2008).

Prior et al., "Analysis of high frequency acoustic emission signals as a new approach for assessing knee osteoarthritis," *Ann Rheum Dis*, 69(5):929-930 (2010).

Protopappas et al., "An Ultrasound Wearable System for the Monitoring and Acceleration of Fracture Healing in Long Bones," *Transactions on Biomedical Engineering*, 52(9): 1597-1608 (2005).

Range et al., "Joint Replacement Programs, Introducing the American Joint Replacement Registry," <http://www.jointcommission.org/> (Nov. 29, 2012).

Rashid et al., "The Sound of Orthopaedic Surgery—The Application of Acoustic Emission Technology in Orthopaedic Surgery: A Review," *European Journal of Orthopaedic Surgery & Traumatology* (2012).

Rowland et al., "Dynamic Health Monitoring Of Metal On Metal Hip Prostheses Using Acoustic Emission," *Proceedings of 2004 DGZFP, BB 90-CD*, Lecture 45, 466-67 (2004).

Ruther et al., "Current Possibilities for Detection of Loosening of Total Hip Replacements and How Intelligent Implants Could Improve Diagnostic Accuracy," *Recent Advances in Arthroplasty*, 364-86 (2012) <http://www.intechopen.com/books/recent-advances-in-arthroplasty/current-possibilities-for-detection-of-loosening-of-total-hip-replacements-and-how-intelligent-impla>.

Salvetti et al., "Editorial: Intelligent Signal and Image Processing in eHealth," *The Open Medical Informatics Journal*, 4:103-4 (2010).

Schwalbe et al., "Nondestructive and Noninvasive Observation of Friction and Wear of Human Joints and of Fracture Initiation by Acoustic Emission," *Proceedings of the Institution of Mechanical Engineers*, 213(1):41 (1999).

Shark et al., "Discovering Differences in Acoustic Emission Between Healthy and Osteoarthritic Knees Using a Four-Phase Model of Sit-Stand-Sit Movements," *The Open Medical Informatics Journal*, 4:116-125 (2010).

Shark et al., "Knee acoustic emission: A potential biomarker for quantitative assessment of joint ageing and degeneration," *Medical Engineering & Physics*, 33:534-545 (2011).

Shrivastava et al., "Assessment of bone condition by acoustic emission technique: a review," *J. Biomedical Science and Engineering*, 2:144-54 (2009).

Singh et al., "Development of Classification and Response Criteria for Rheumatic Diseases," *Arthritis & Rheumatism (Arthritis Care & Research)*, 55(3):348-52 (2006).

Singh, "Epidemiology of Knee and Hip Arthroplasty: A Systematic Review," *The Open Orthopaedics Journal*, 5:80-5 (2011).

Solomon et al., "Contribution of Hospital Characteristics to the Volume-Outcome Relationship," *Arthritis & Rheumatism*, 46(9):2436-44 (2002).

Sugiyama et al., "Examination of Rotational Fixation of the Femoral Component in Total Hip Arthroplasty," *Clinical Orthopaedics & Related Research*, 249:122-28 (1989).

Unger et al., "Acoustic Monitoring (RFM) of Total Hip Arthroplasty Results of a Cadaver Study," *European Journal of Medical Research*, 14(6):264-271 (2009).

Vad et al., "Managing Knee Osteoarthritis: Rationale for Early Treatment," *The Journal of Musculoskeletal Medicine*, 29(6) (2012) (7 pages).

Wright et al., "Acoustic Emission: A Non-invasive Monitoring Technique for Total Joint Replacement Patients," *J. Biomechanics*, 16(4):295 (1983).

www.acousticemission.net, "Medical Applications for Acoustic Emission," Cardiff University, 2 pp. (2006), accessed Mar. 4, 2013.

www.healio.com, "New Device Could Predict Impending Stress Fractures Through Acoustic Emissions," Orthopedics Today, 4 pp. (Nov. 2006), accessed Mar. 4, 2013.

Zhang et al., "EULAR evidence-based recommendations for the diagnosis of knee osteoarthritis," *Ann Rheum Dis*, 69:483-9 (2010).

Zolog, "Acoustic Emission Measurement System in Diagnostic of Cartilage Injuries of the Knee," (2011) (unpublished Dr. Med. Thesis, Philips-Universatät Marburg (on file with Philips-Universatät Marburg Library).

Popescu et al., "An acoustic fall detector system that uses sound height information to reduce the false alarm rate," 30th Annu. Int. Conf. IEEE Eng. Med. Biol. Soc. Conference, Vancouver, British Columbia, Canada pp. 4628-4631 (2008).

\* cited by examiner

IMPLANT EVALUATION USING ACOUSTIC EMISSIONS

CROSS-REFERENCE TO RELATED APPLICATION

This application is a continuation of U.S. Nonprovisional application Ser. No. 16/206,604 filed Nov. 30, 2018, which claims the benefit of U.S. Provisional Application No. 62/593,210, which was filed Nov. 30, 2017, the entireties of which are herein incorporated by reference.

FIELD

The present disclosure provides methods of identifying a loosened joint implant by analyzing acoustic emissions from the implant. The present disclosure further provides apparatuses for measuring acoustic data and analyzing acoustic emissions from a joint implant.

BACKGROUND

Total knee arthroplasty (TKA) has become a routine and successful surgical procedure. Over 95 percent of total knee replacements in the United States are performed for osteoarthritis. As of 2010, over 600,000 total knee replacements were being performed annually in the United States. The number of total knee replacements performed annually in the United States is expected to grow by 673 percent to 3.48 million procedures by 2030.

Failure of TKAs is considered as two groups. Problems within the first two years are considered early failures and typically a patient will have problems starting shortly after the surgery. Failures that occur after two years are considered late failures. The top three causes of failure are (1) infection, (2) instability, and (3) aseptic loosening. Infection can be detected by testing blood or fluid extracted from the joint region. Instability can be diagnosed by evaluation of gait and movement of the joint. The best current practice for diagnosing loosening is identification of a gap between the bone and implant on an x-ray image, which is considered definitive only after 30% of the bone around the implant has been lost. The cost and risk of revision surgery to correct a failed implant rises significantly as the damage becomes more advanced.

SUMMARY

In an aspect, the present disclosure provides for, and includes, a method of identifying a loosened implant in a joint, the method comprising the steps of: positioning a plurality of acoustic sensors at a respective plurality of locations around the joint, causing the joint to be moved, receiving signals from the acoustic sensors during the movement of the joint, identifying signals from two or more of the plurality of acoustic sensors that correspond to a common acoustic event, identifying a position of the acoustic event within the joint, and providing a health indication related to the joint.

In an aspect, the present disclosure provides for, and includes, a method of identifying a position comprising: calculating a first time delay between a first time of receipt of a first signal from a first acoustic sensor of the plurality of acoustic sensors and a second time of receipt of a second signal from a second acoustic sensor of the plurality of acoustic sensors, and calculating a first geometric surface of possible locations of the acoustic event from the first time delay. In one aspect, a method of identifying a position further comprises: calculating a second time delay between the first time of receipt and a third time of receipt of a third signal from a third acoustic sensor of the plurality of acoustic sensors, calculating a second geometric surface of possible locations of the acoustic event from the second time delay, and determining a line of intersection of the first and second geometric surfaces. In an aspect, a method of identifying a position further comprises determining where the first geometric surface intersects the implant.

In an aspect, the present disclosure provides for, and includes, a method of identifying a position comprising: calculating a first magnitude difference between a first signal amplitude of a first signal from a first acoustic sensor of the plurality of acoustic sensors and a second signal magnitude of a second signal from a second acoustic sensor of the plurality of acoustic sensors, and calculating a first geometric surface of possible locations of the acoustic event from the first amplitude difference. In one aspect, a method of identifying a position further comprises adjusting the first time delay according to predetermined speeds of signal propagation within each of the one or more types of tissue and the signal paths.

In an aspect, the present disclosure provides for, and includes, a method of calculating a first time delay comprising: identifying one or more types of tissue between the implant and the first acoustic sensor, identifying one or more signal paths from the implant to the first acoustic sensor, and adjusting the first time delay according to predetermined speeds of signal propagation within each of the one or more types of tissue and the signal paths.

In an aspect, the present disclosure provides for, and includes, a method of identifying a loosened implant in a joint, comprising the steps of: positioning an acoustic sensor at a location proximate to the joint, causing the joint to be moved, receiving a signal from the acoustic sensor during the movement of the joint, analyzing the signal to identify an attribute that is associated with a state of joint health, and providing a health indication related to the joint.

In one aspect, the present disclosure provides for, and includes, a method of analyzing a signal comprising calculating a rise time and a magnitude from the signal, comparing the rise time to a first threshold and the magnitude to a second threshold, and determining that the signal is indicative of a loose implant when the rise time exceeds the first threshold and the magnitude exceeds the second threshold. In an aspect, methods of analyzing a signal in the present disclosure are performed only when the signal comprises a primary frequency within a predetermined band.

In an aspect, the present disclosure provides for, and includes, a method of analyzing a signal comprising calculating a power spectral density (PSD) of the signal, calculating a first partial power of the PSD within a predetermined first frequency band, comparing the first partial power to a first threshold, and determining that the signal is indicative of a loose implant when the first partial power exceeds the first threshold.

In an aspect, the present disclosure provides for, and includes, a method of analyzing a signal comprising calculating a power spectral density (PSD) of the signal, calculating a first partial power of the PSD within a predetermined first frequency band, calculating a second partial power of the PSD within a predetermined second frequency band, and comparing the first partial power to the second partial power. In one aspect, a comparison of the first partial power to the second partial power comprises calculating a ratio of the first partial power to the second partial power, and determining that the signal is indicative of a loose implant when the ratio exceeds a threshold. In an aspect, a comparison of the first partial power to the second partial power comprises calculating a difference between the first partial power and the second partial power, and determining that the signal is indicative of a loose implant is loose when the difference exceeds a threshold.

In an aspect, the present disclosure provides for, and includes, a method of analyzing a signal comprising calculating a power spectral density (PSD) of the signal, calculating a first maximum value of the PSD within a predetermined first frequency band, calculating a second maximum value of the PSD within a predetermined second frequency band, and comparing the first maximum value to the second maximum value.

In an aspect, the present disclosure provides for, and includes, a method of providing a health indication related to the joint comprising evaluating the total number of acoustic events indicative of a loose implant to determine a diagnostic indication of a loose implant.

In an aspect, the present disclosure provides for, and includes, an apparatus for identifying a loosened implant in a joint, the apparatus comprising the steps of: a plurality of acoustic sensors configured to be placed in contact with a patient's skin at a respective plurality of locations around the joint, a processor configured to receive signals from the acoustic sensors during the movement of the joint, where the processor is configured to: identify signals from two or more of the plurality of acoustic sensors that correspond to a common acoustic event, compare an attribute of the signals, identify a position of the acoustic event within the joint, and provide a health indication related to the joint.

BRIEF DESCRIPTION OF THE DRAWINGS

Aspects of the disclosure are herein described, by way of example only, with reference to the accompanying drawings. With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figures 1A, 1B:
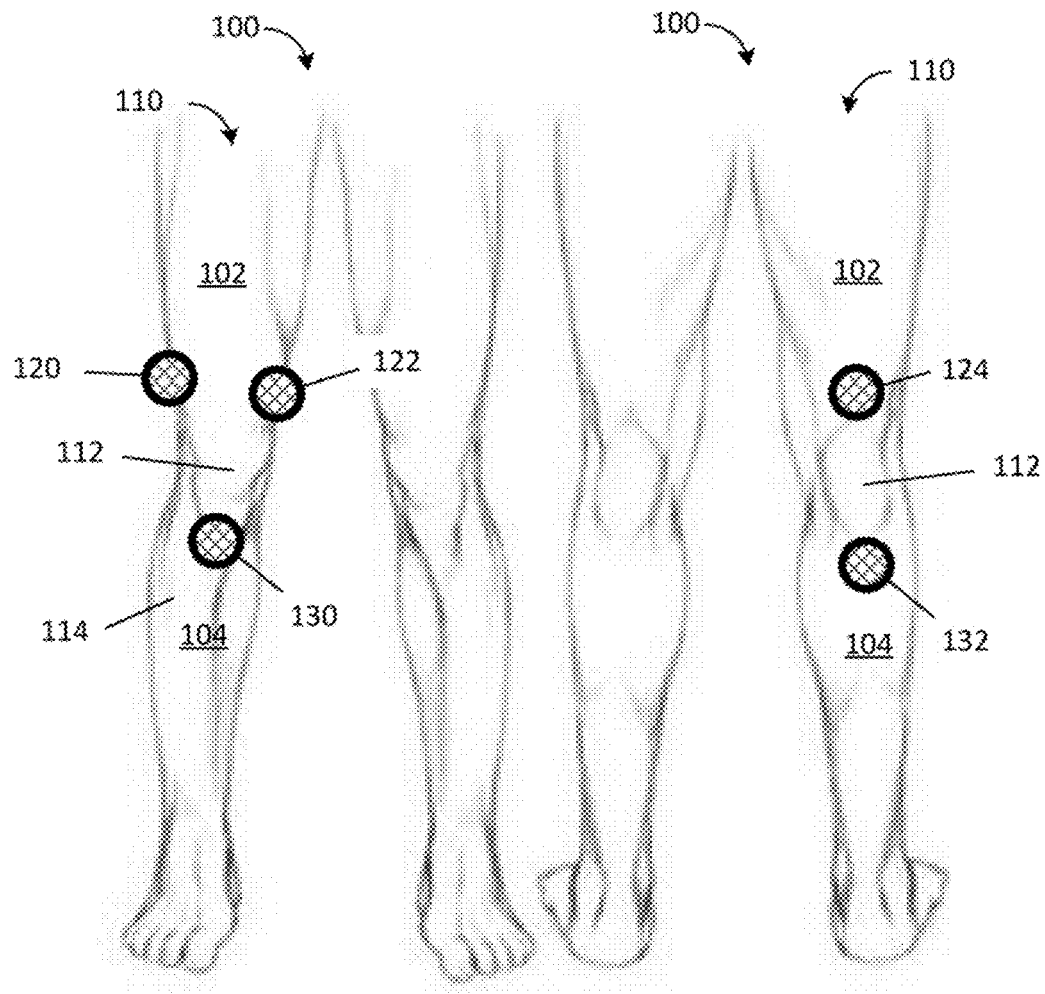
FIGS. 1A and 1B are front and rear views of a patient's legs while the right leg is being evaluated for loosening, in accordance with the present disclosure.

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations, and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an," and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or an acoustic measurement and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, a "patient" may be a human or animal subject.

As used herein, "tissue" includes all biologic material within a body, including bone, ligaments, tendons, cartilage, and muscle.

As used herein, "lossy" refers to the characteristic of material that causes high attenuation or dissipation of energy.

The methods of the present disclosure differ from existing algorithms for analyzing acoustic signals, for example, the methods provided in U.S. Publication No. 2016/0015319 involving enveloping functions and vector functions. Specifically, the '319 Publication implemented a data analysis approach whereby each waveform was analyzed in the time-domain with a waveform enveloping function (Hilbert transform). The envelopes were categorically segregated into distinct types that were segregated using a vector function associated with health status. On the other hand, the methods of the present disclosure analyze acoustic events with signals captured on multiple sensors. These signals are more robust, less likely to be due to noise effects (i.e. triboelectric effect, sensor-skin rubbing), and are amendable to localization. The methodology of the present disclosure also analyzes signals that extend beyond the time-domain, featuring power spectral analysis. Without being limited by theory, loose implants have an increased ability to vibrate, with the degree of possible vibration and the damping of a natural vibration (frequency resonance) relating to the degree of looseness. The methodology of the present disclosure include an analysis of specific frequency magnitudes, partial powers (specific frequency band powers), and signal fall times to derive an indication of the likelihood of a loosened implant.

In one aspect, acoustic measurements of the present disclosure can be collected by an apparatus a plurality of acoustic sensors configured to be placed in contact with a patient's skin at a respective plurality of locations around the joint, a processor configured to receive signals from the acoustic sensors during the movement of the joint, where the processor is configured to: identify signals from two or more of the plurality of acoustic sensors that correspond to a common acoustic event, compare an attribute of the signals, identify a position of the acoustic event within the joint, and provide a health indication related to the joint. In an aspect, acoustic measurements of the present disclosure can be collected by an Orthosonos device. In an aspect, two or more signals from two or more of the plurality acoustic sensors are identified as corresponding to a common acoustic event if they occur within a short enough timeframe, such as within about 0.01 seconds, within about 0.005 seconds, within about 0.004 seconds, within about 0.003 seconds, within about 0.0025 seconds, within about 0.002 seconds, within about 0.0015 seconds, or within about 0.001 seconds.

FIGS. 1A and 1B are front and rear views of a patient's legs 100 while the right leg 110 is being evaluated for loosening, in accordance with the present disclosure. In an aspect, the right knee 112 has an implant (not visible in FIGS. 1A and 1B) and is being evaluated. In one aspect, three sensors 120, 122, and 124 have been placed at approximately evenly distributed positions around the right thigh 102 above the knee 112 and two sensors 130 and 132 have been placed on the anterior and posterior sides of calf 104 below the knee 112. In an aspect, the number of sensors placed on either the thigh 102 or calf 104 is typically in the range of 1 to 8, but may be any number of sensors and arranged in any pattern with both vertical and circumferential spatial separation, such as from 1 to 4, from 1 to 6, from 2 to 8, and from 4 to 8. In an aspect, the sensors placed around either the thigh 102 or calf 104 are evenly distributed. In an aspect, the sensors placed around either the thigh 102 or calf 104 may have different separation distances. In an aspect, a pair of sensors, for example sensors 130 and 132, are placed on opposite sides of a thigh 102 or calf 104. In an aspect, a pair of sensors, for example sensors 120 and 122, are closer to one side of the leg 110. In an aspect, the location of a sensor may be selected for improved coupling to the bone. In one aspect, sensor 130 is positioned directly over the tibia (not visible in FIG. 1A). In an aspect, sensor 130 may be repositioned to avoid inflicting pain on a patient. In one aspect, sensor 130 may be repositioned to sit flush against the skin of a patient. In an aspect, sensor 130 may be repositioned to accommodate the unique shape of a patient's joint.

Although the figures shown herein are primarily associated with knee implants, the same methods and apparatus can be successfully applied to the evaluation of implants in other joints, for example hips, spines, and shoulders. Nothing in this application should be construed to limit the application of the disclosed methods and apparatus to a particular joint or type of implant or to limit the application to humans.

Figure 1C:
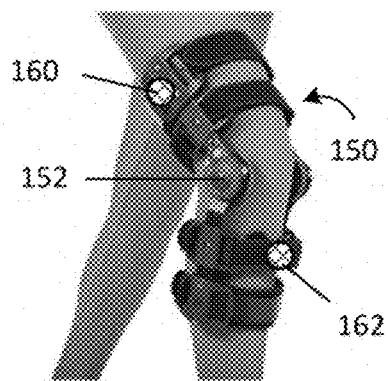
FIG. 1C depicts an example sensor assembly, in accordance with the present disclosure.

FIG. 1C depicts another example sensor assembly 150, in accordance with the present disclosure. The design and construction of assembly 150 are illustrative and alternate arrangements are included in the concept, including assemblies that mount only above or below the joint, assemblies that are adhered locally around a sensor location, sensors that are temporarily taped or otherwise held in a position proximate the joint, and other harnesses and attachments as will be known to those of skill in the art. Assemblies 150 that perform equivalent functions for positioning acoustic sensor proximate to joints other than the knee are included in the various aspects of assembly 150.

In an aspect, acoustic sensors are placed at locations 160 and 162. In an aspect, the acoustic sensors at locations 160, 162 are held in contact with the skin by the assembly 150. In an aspect, the acoustic sensors are acoustically coupled to the tissue at the locations 160, 162. In an aspect, acoustic sensors are placed in contact with the skin of a patient at one or more locations not shown in FIG. 1C. In an aspect, the assembly 150 comprises a hinge 152 to control the positioning of sensor locations 160, 162 relative to the knee. In an aspect, the sensor assembly 150 is worn for a diagnostic regime of defined motions, for example moving from a sitting position to a standing position or climbing a set of stairs. In one aspect, the sensor assembly 150 is worn for a period of normal activity, where the sensor assembly 150 comprises a data collection and storage capability to acquire and retain signals from the acoustic sensors until the data records are uploaded to a computer or other data storage system.

Figure 1D:
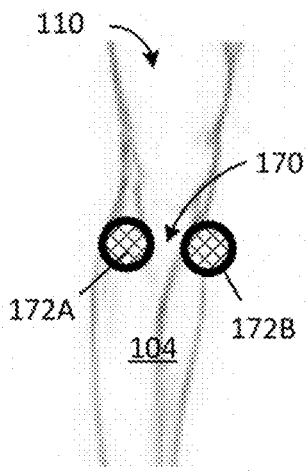
FIG. 1D is a front partial view of a patient's leg while being evaluated for loosening, in accordance with the present disclosure.

FIG. 1D is a front partial view of a patient's leg 110 while being evaluated for loosening, in accordance with the present disclosure. In an aspect, acoustic sensors 172A and 172B are placed on the skin proximal to the medial and lateral condyle adjacent to the anterior tibial crest 170 of calf 104.

Figure 1E:
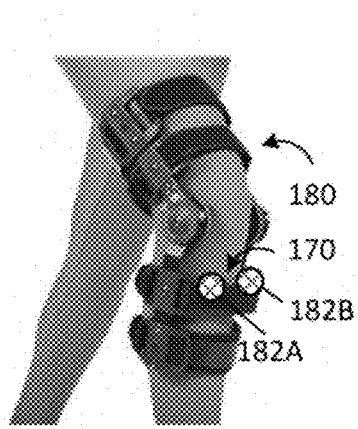
FIG. 1E depicts another example sensor assembly, in accordance with the present disclosure.

FIG. 1E depicts another sensor assembly 180, in accordance with the present disclosure. Sensors 182A and 182B are located on the assembly 180 such that the two sensors 182A, 182B are kept in contact with the skin of the calf 104 medial and lateral of the anterior tibial crest 170.

Figure 2:
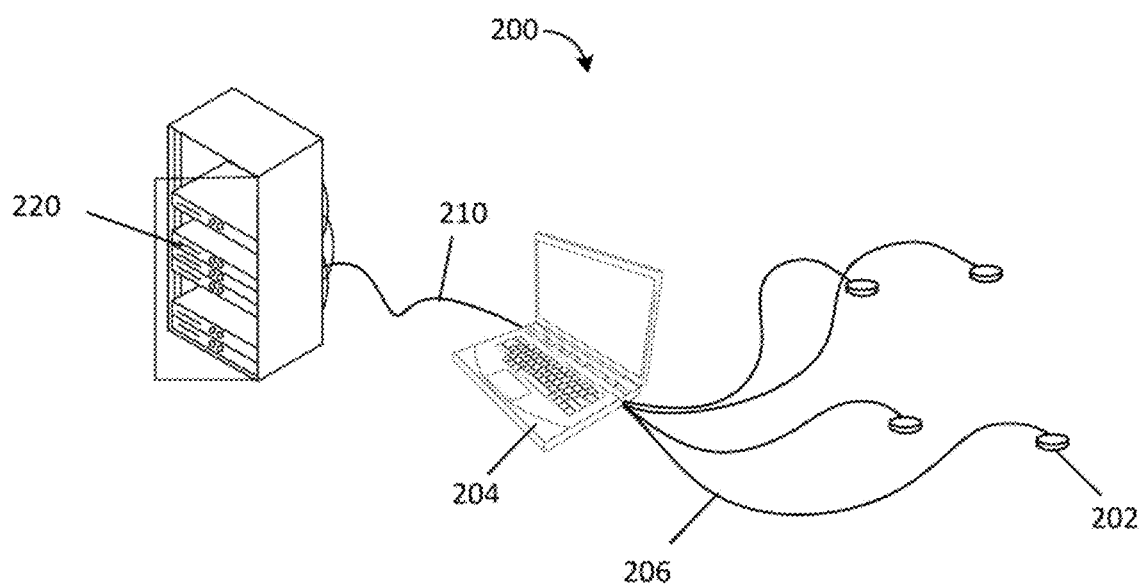
FIG. 2 depicts an implant assessment system, in accordance with the present disclosure.

FIG. 2 depicts an implant assessment system 200, in accordance with the present disclosure. In one aspect, there are four acoustic sensors 202 connected via cables 206 to a processor 204. In an aspect, the sensors 202 communicate wirelessly with the processor 204. In an aspect, the sensors 202 comprise a memory to store signals and later upload the recorded signals to the processor 204. In an aspect, the processor 204 comprises a data collection system (not shown in FIG. 2) configured to receive the signals from the acoustic sensors and convert them to digital data. In an aspect, the processor 204 comprises a memory (not shown in FIG. 2) configured to store a portion of the digital data produced from signals received from the acoustic sensors 202. In an aspect, the processor 204 may be coupled to other systems or programs in place of the server 220, for example a cloud-based storage system or an electronic medical record.

In an aspect, the processor 204 is coupled to a server 220 as illustrated by cable 210. In an aspect, the cable 210 comprises a communication network (not shown in FIG. 2) that may include network switches, hubs, wired or wireless communication paths such as Bluetooth and Ethernet and wifi, wireless access points, and nonvolatile storage devices that can be selectively coupled to the processor 204 and server 220. In an aspect, the server 220 comprises a database in which is stored the digital data or attributes of the digital data.

Determining a state of health of a joint having a partial or total replacement with an implant, or a healthy joint, through analysis of acoustic signals as described herein is different from other methods of evaluation that are commonly used to assess joints, for example computerized axial tomography (CAT or CT) scanning and medical ultrasound.

CAT scanning emits electromagnetic radiation in the X-ray frequencies that pass through the patient to a receiver that measures the received X-ray. Measurements are taken from different angles to produce cross-sectional images of specific areas. In contrast, the apparatus and methods disclosed herein utilize passive acoustic transducers to capture pressure waves generated within the body, and therefore they do not emit energy, do not form an image, the transducers do not move relative to the patient during a single evaluation session, and signals are primarily analyzed for direct indications of joint failure and not for the purposes of tissue imaging.

Medical ultrasound creates images also known as sonograms. Sonograms are generated by using a probe to send pulses of ultrasound into tissue where the sound echoes off the various elements of the tissue, with different tissues reflecting varying degrees of sound. The ultrasound transducer then captures the reflected signal and determines the timing and strength of the signals. In the A-mode, the transducer scans a single line and plots the varying response along this line. In the B-mode, a linear array of transducers in the probe are arranged to produce an image of a two-dimensional (2D) plane through the tissue. In C-mode, the reflected signal is gated to form a planar image at a defined depth. Ultrasound is effective for imaging soft tissues of the body. In contrast, the apparatus and methods disclosed herein utilize passive acoustic transducers and do not emit energy, do not form an image, the transducers do not move relative to the patient during a single evaluation session, and acoustic signals are primarily analyzed for direct indications of joint failure and not for the purposes of tissue imaging.

Figure 3:
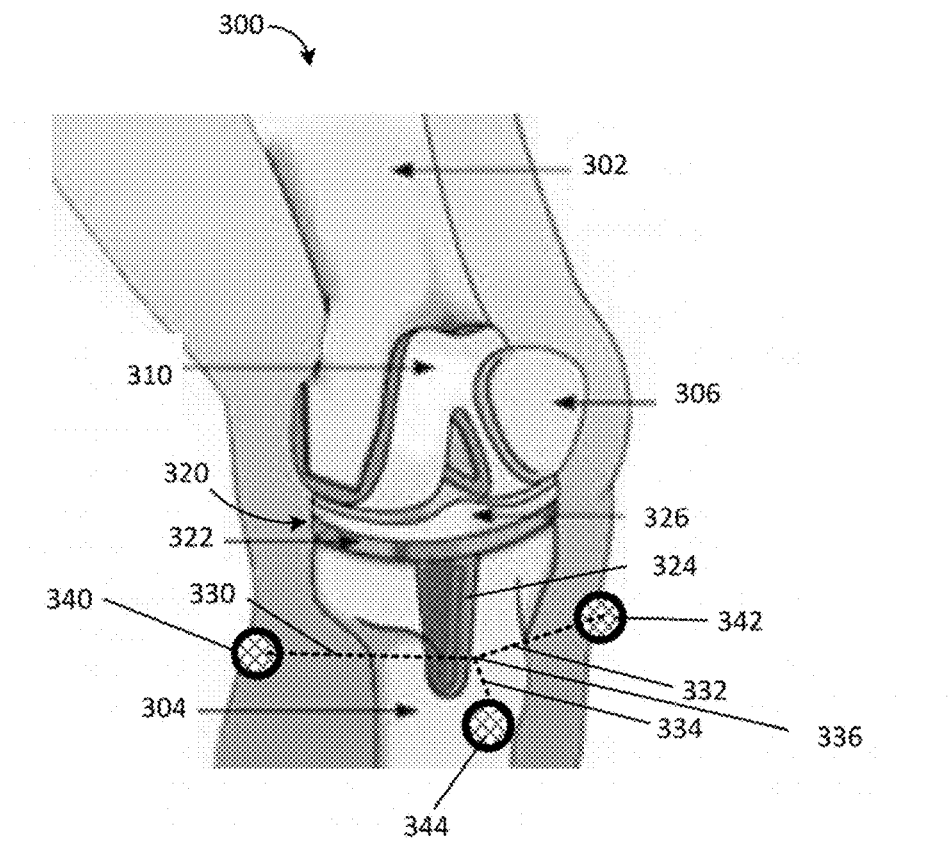
FIG. 3 is an illustration of a knee with an implant and acoustic sensors, in accordance with the present disclosure.

FIG. 3 is an illustration of a knee 300 with an implant 320 and acoustic sensors 340, 342, and 344, in accordance with the present disclosure. This implant 320 has a femoral component 310 adhered to the femur 302, a tibial component 322 with a stem 324 that extends into the tibia 304, and a spacer 326. In an aspect, natural patella 306 can be retained.

In an aspect, the three acoustic sensors 340, 342, 344 are located in a common horizontal plane and at various positions around the knee, separated from an acoustic event source 336 by distances 330, 332, and 334. In an aspect, the distances 330, 332, 334 are not equal. In another embodiment, the plane is not horizontal. In an aspect, the acoustic event source 336 is at the interface between the tibia 304 and the stem 324.

When an acoustic event occurs at source 336, a "shock wave," also referred to as an acoustic signal, propagates outward from source 336 in all directions. The shock wave propagates at a speed that is associated with the material through which the shock wave is passing. The attenuation of the shock wave is also associated with the material. In an aspect, the attenuation of the shock wave while it passes through the metal of the stem 324 is lower, e.g., the signal retains its strength, than when the shock wave passes through soft tissue. Similarly, the speed of the shock wave will be higher in the metal stem 324 than in the soft tissue.

Each path 330, 332, 334 will have a different overall length as well as different materials in the path. In one aspect, path 330 passes through the stem 324, the tibia 304, and soft tissue, while paths 332, 334 pass through only bone and soft tissue. In an aspect, a shock wave initiated at source 336 will arrive at each of acoustic sensors 340, 342, and 344 at different times, referred to as the "time of flight" for that path, and with different signal amplitudes.

A location of source 336 can be calculated using one or both of the differences in arrival time and differences in amplitude of the received signals at acoustic sensors 340, 342, 344. If the material between the source 336 and sensors 340, 342, 344 were homogeneous, spheres of possible locations could be modeled around each of sensors 340, 342, 344 with different diameters based on the differences in arrival time plus a common offset duration. The common offset duration is increased until the three spheres intersect at a single point, which is the estimate of the location of source 336. In a knee or other joint, however, the structure is not homogeneous. A computer model must be used to model the locations of the acoustic sensors 340, 342, 344 on the joint as well as the structure and composition of the underlying tissue. Surfaces can be modeled around each of sensors 340, 342, 344 with different shapes that reflect the material between the sensor and the surface, and a point of intersection can be identified as before. In an aspect, the estimated position of the source 336 is determined when the three surfaces pass within a defined distance of each other, as there may be no single point where all three surfaces intersect for a common offset duration.

Similarly, the shape and size of the spheres modeled around each of the sensors 340, 342, 344 may be determined using the relative amplitudes of the signals received at the respective sensors 340, 342, 344. In general, the amplitude of a signal will be attenuated more when it has passed through a greater thickness of tissue or a more lossy tissue, such as muscle compared to bone.

In an aspect, additional acoustic sensors (not shown in FIG. 3) may be placed on the thigh around the femur 302 and detect signals originating from source 336, in which case the acoustic paths may pass through one or more of the tibial component 322, the spacer, 326, the femoral component 310, and the femur 302. In an aspect, there are multiple paths between the source 336 and an acoustic sensor, such as sensor 340, and a signal emanating from source 336 may arrive at different times and with different amplitudes having been conducted along these multiple paths. In an aspect, analysis will determine signal characteristics that are associated with only one of the multiple signals that are received by the sensor.

Figure 4A:
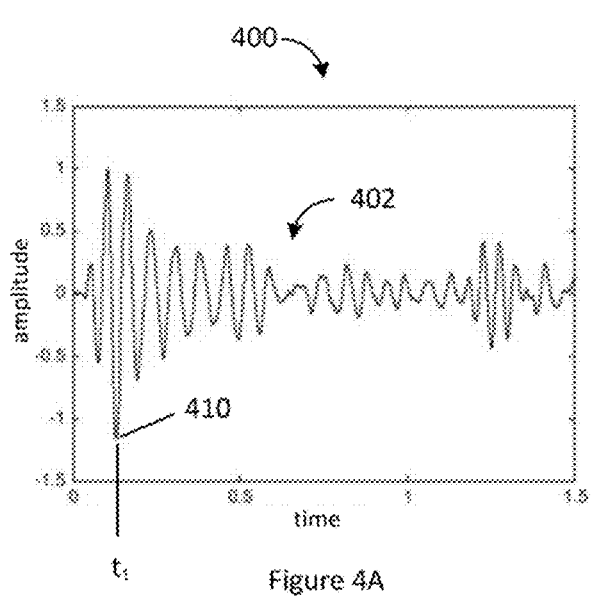
FIGS. 4A and 4B are plots of the signals from two spatially separated acoustic sensors, in accordance with the present disclosure.
Figure 4B:
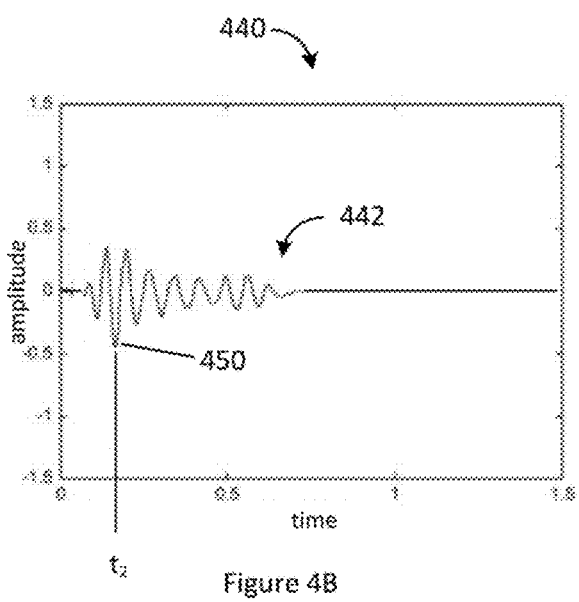

FIGS. 4A and 4B are plots 400, 440 of signals 402, 442 received by two spatially separated acoustic sensors, in accordance with the present disclosure. Signal 402 has a maximum amplitude at peak 410 that occurs at time $t_1$. Signal 402 has a corresponding maximum amplitude at peak 450 that occurs at time $t_2$. The signal processing electronics of system 200, shown in FIG. 2, will compare one or more aspects of signals 402, 442 to determine whether they are a common signal. In an example, signals 402, 442 originated from a common acoustic event. As the maximum amplitude of signal 442, at peak 450, is smaller than the maximum amplitude of signal 402, at peak 410, the source of the common signal is likely farther from the sensor of signal 442 than the sensor of signal 402. This relative distance will also be evident in the difference between times $t_1$ and $t_2$.

Figure 5A:
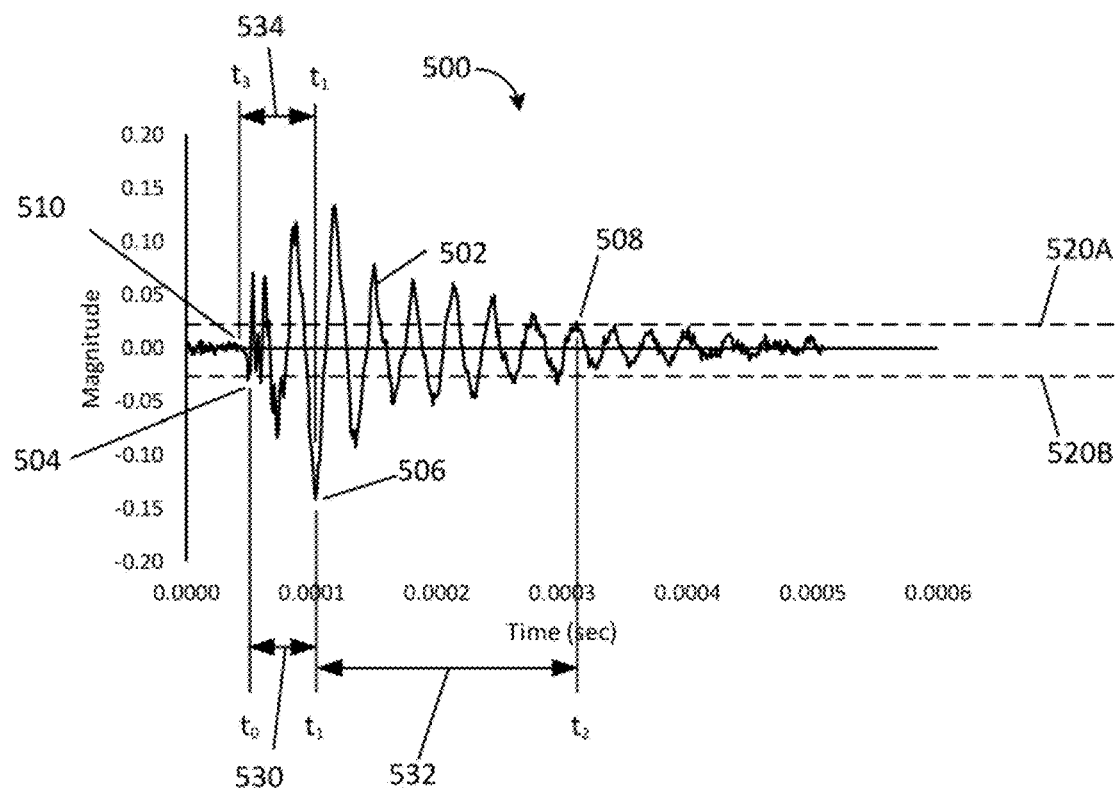
FIG. 5A depicts attributes of a representative acoustic signal, in accordance with the present disclosure.

FIG. 5A depicts attributes of a representative acoustic signal 502, in accordance with the present disclosure. A threshold with upper limit 520A and a lower limit 520B has been established around the average signal, which is zero in FIG. 5A. The signal 502 exceeds the threshold at point 504, where signal 502 crosses the lower limit 520B. The signal 502 has a peak amplitude at point 506 and then is attenuated over time until the last excursion of signal 502 outside the threshold is at point 508 where signal 502 crosses the upper limit 520A. "Rise time" 530, 'time from the first threshold crossing to highest voltage point on the waveform', is defined as the time interval from point 504, time $t_0$, to point 506, time $t_1$. In an aspect, the signal processing electronics determines that the first deviation of signal 502 from the prior noise was at point 510, time $t_3$, and the rise time of signal 502 is computed using time interval 534 between point 510 and 506.

"Fall time" 532, 'time from highest voltage point on the waveform to last threshold crossing,' is defined as the time interval from point 506 to point 508, time $t_2$. In an aspect, the fall time is determined using a different feature of signal 502, for example the last detectable sine wave at the principal frequency of signal 502.

In an aspect, one or both of the rise time and fall time are related to a natural frequency of one of the components of an implant, for example the tibial component 322 of FIG. 3. Every physical object has multiple resonant frequencies that are associated with various bending modes of that object when unconstrained. The lowest resonant frequency is referred to as the primary natural frequency, commonly called "the natural frequency." The natural frequency of an item can often be determined by suspending the item using a light, non-extensible, flexible line, for example—a fishing line, and providing an impulse stimulus, for example a classic "pencil lead break" force.

A fully attached implant will be restrained from vibrating at its natural frequency by the surrounding bone and cement. A loose implant, however, will have some ability to vibrate, with the degree of possible vibration and the damping of a natural vibration related to the degree of looseness. Thus, the peak amplitude of signal 502 and the fall time 532 are attributes of signal 502 that are related to the looseness of the implant in the joint being assessed.

In an aspect, the signal 502 between time $t_0$ and time $t_2$ is considered to be associated with "an acoustic event" caused by a mechanical interaction between elements of the implant, proximate bones, and adjacent tissue. Such mechanical interaction may include friction between surfaces of adjacent tissues, friction between elements of the implant, or movement and impact between an element of the implant and a bone. Healthy tissue has a background level of acoustic events, for example from motion between a ligament and a bone surface.

In an aspect, the number of acoustic events is indicative of the health of a joint. Healthy joints will have fewer and lower-magnitude acoustic signals, compared to a failing joint. The total number of acoustic events captured while a person performs a set motion sequence is included as a component in the algorithmic computation for the indication of joint loosening.

Figure 5B:
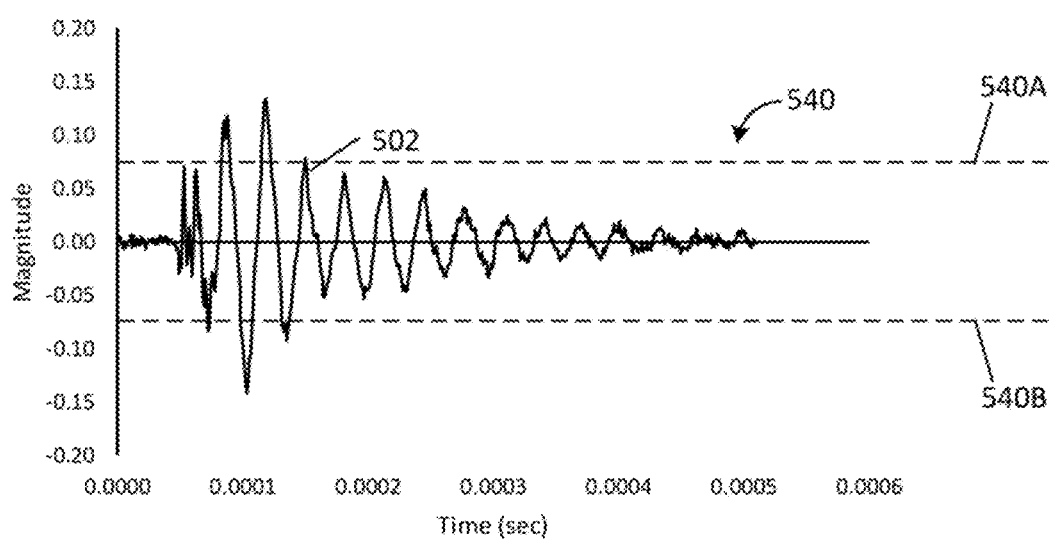
FIG. 5B depicts a threshold for analysis of the acoustic signal of FIG. 5A, in accordance with the present disclosure.

FIG. 5B depicts a threshold 540 for analysis of the acoustic signal 502 of FIG. 5A, in accordance with the present disclosure. Threshold 540 has an upper limit 540A and a lower limit 540B. The limits 540A, 540B are different from limits 520A, 520B of FIG. 5A in that signals that exceed limits 520A, 520B are determined to be acoustic events, instead of background noise, while signals that exceed limits 540A, 540B are determined to be acoustic events associated with a particular joint health condition. In an aspect, a signal 502 that exceeds threshold 540 is associated with a loose implant.

In an aspect, threshold 540 is determined based off the observed data recorded from patients who either had a healthy or loose implant, following an optimization function to where the greatest number of failed implants contained acoustic events that crossed such threshold and healthy implants had the fewest number of events that crossed the threshold.

Figure 6:
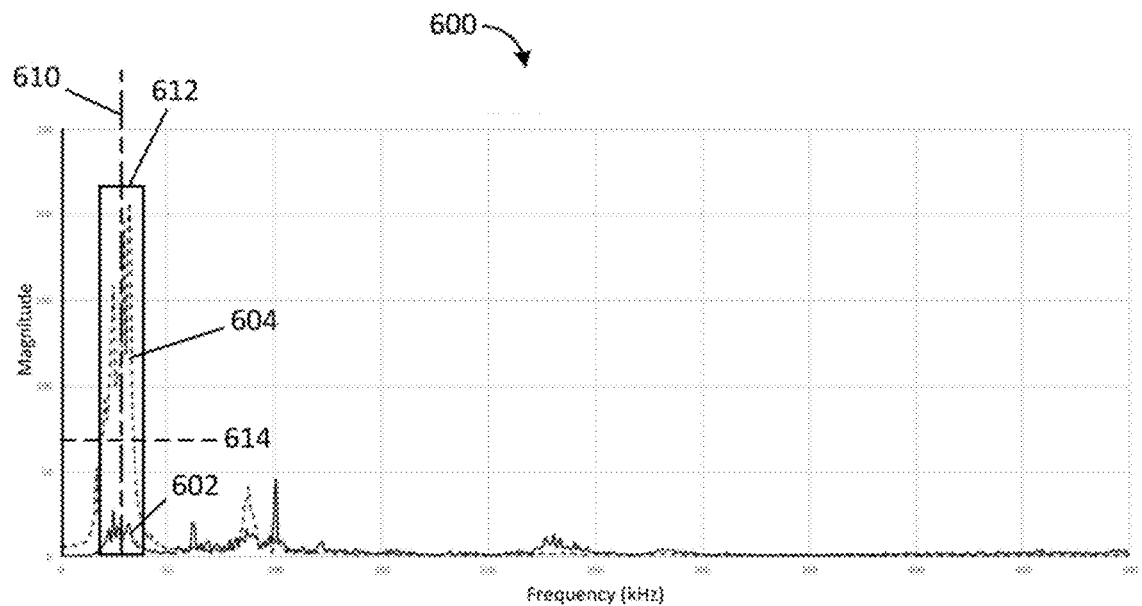
FIG. 6 depicts a method of detecting loosening of an implant by an increase in the magnitude of a resonant frequency, in accordance with the present disclosure.

FIG. 6 depicts a method of detecting loosening of an implant by an increase in the magnitude of a resonant frequency, in accordance with the present disclosure. Plot 600 shows the PSD 602 (solid line) of an example signal acquired by an acoustic sensor, for example as shown in FIGS. 1A and 1B, from a "healthy" implant and PSD 604 (dashed line) of an example signal acquired by an acoustic sensor from a "failed" implant. The PSDs are generated using Fast Fourier Transforms (FFTs) of the received signal, for example signal 502 of FIGS. 5A and 5B. In an aspect, both implants are of a similar design and known to have a natural frequency 610. A frequency band 612, also referred to as a "window," has been selected that encompasses the natural frequency 610. In one aspect, the frequency band 612 extends from approximately 20 kHz to 40 kHz.

The PSD 602 has several modest peaks within the frequency band 612. The PSD 604 of the failed implant shows much larger peaks within the frequency band 612. In an aspect, the maximum magnitude of the peaks within the frequency band 612 is compared to a threshold 614, where a magnitude that exceeds the threshold 614 is an indication that the associated implant is damaged. In an aspect, a ratio of the magnitude of PSD 604 to the magnitude of PSD 602 is compared to a threshold. In an aspect, the area under the PSD 604 within the frequency band 612, referred to as the "partial power," is compared to the partial power of PSD 602 within frequency band 612. In an aspect, the ratio of the partial powers is compared to a threshold. In an aspect, the difference between the partial powers is compared to a threshold.

In another aspect, PSD 602 is associated with a baseline acoustic signal measured shortly after the surgery and PSD 604 is associated with an acoustic signal measured on the same joint after a period of time has elapsed. This approach has the advantage of avoiding person-to-person variations in the details of the implant surgery and resultant joint structure.

Figure 7:
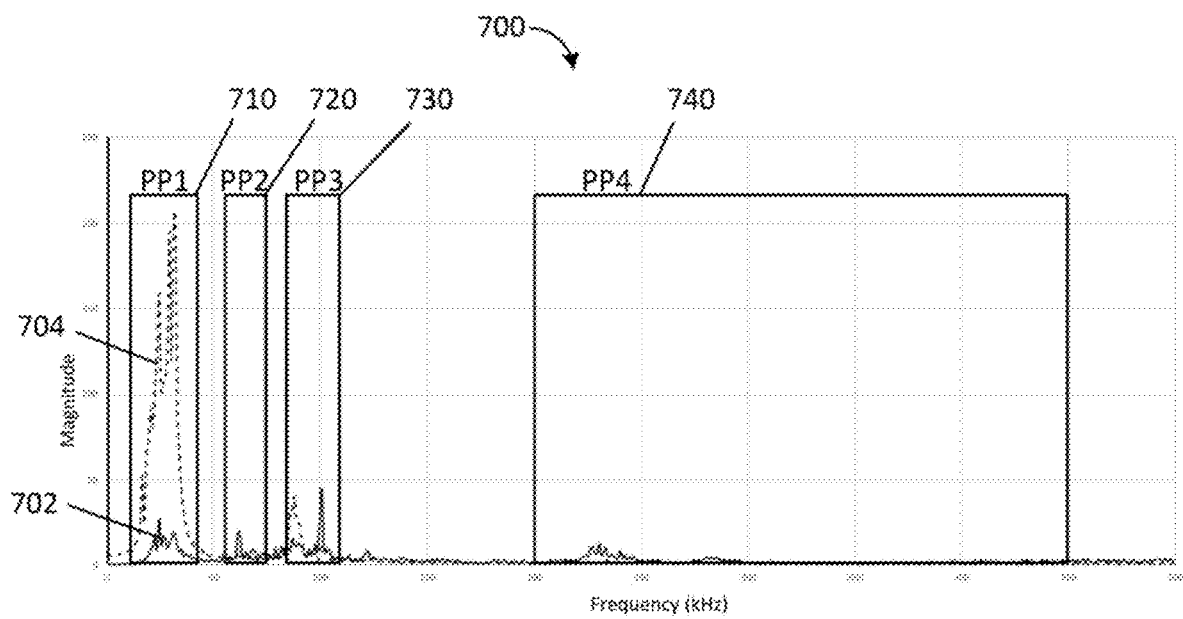
FIG. 7 depicts a method of detecting loosening of an implant by evaluation of the partial powers of frequency windows, in accordance with the present disclosure.

FIG. 7 depicts a method of detecting loosening of an implant by evaluation of the partial powers of signals 702, 704 within frequency windows, in accordance with the present disclosure. In an aspect, four frequency bands 710, 720, 730, and 740 have been defined. Each of signals 702 (solid line), 704 (dashed line) has a partial power associated with each window 710, 720, 730, and 740. In an aspect, the partial powers of signals 702, 704 within a common window are compared, either by ratio or difference. In an aspect, a ratio of the partial powers of signal 702 in two windows, for example windows 710 and 730, is compared to the same ratio of the partial powers of signal 704 in the same windows. This has a normalizing effect, as a window, for example 740, can be predetermined to capture a baseline signal that is not related to looseness. In an aspect, the frequency bands are not the same width.

In an aspect, the frequency limits of partial power band 710 are from 17 Hz to 42 Hz. In one aspect, the frequency limits of partial power band 710 are from 5 Hz to 55 Hz, such as from 5 Hz to 50 Hz, from 5 Hz to 45 Hz, from 10 Hz to 55 Hz, from 10 Hz to 50 Hz, from 10 Hz to 40 Hz, from 15 Hz to 55 Hz, from 15 Hz to 50 Hz, from 15 Hz to 45 Hz, from 5 Hz to 42 Hz, from 10 Hz to 42 Hz, from 15 Hz to 42 Hz, from 17 Hz to 45 Hz, from 17 Hz to 50 Hz, or from 17 Hz to 55 Hz. In an aspect, the frequency limits of partial power band 720 are from 55 Hz to 75 Hz. In one aspect, the frequency limits of partial power band 720 are from 45 Hz to 80 Hz, such as from 45 Hz to 75 Hz, from 50 Hz to 75 Hz, from 55 Hz to 80 Hz, from 60 Hz to 80 Hz, from 65 Hz to 80 Hz, from 70 Hz to 80 Hz, from 75 Hz to 80 Hz, from 55 Hz to 70 Hz, from 55 Hz to 65 Hz, or from 55 Hz to 60 Hz. In an aspect, the frequency limits of partial power band 730 are from 80 Hz to 105 Hz. In one aspect, the frequency limits of partial power band 730 are from 75 Hz to 200 Hz, such as from 75 Hz to 190 Hz, from 75 Hz to 180 Hz, from 75 Hz to 170 Hz, from 75 Hz to 160 Hz, from 75 Hz to 150 Hz, from 75 Hz to 140 Hz, from 75 Hz to 130 Hz, from 75 Hz to 120 Hz, from 75 Hz to 110 Hz, from 75 Hz to 105 Hz, from 80 Hz to 200 Hz, such as from 80 Hz to 190 Hz, from 80 Hz to 180 Hz, from 80 Hz to 170 Hz, from 80 Hz to 160 Hz, from 80 Hz to 150 Hz, from 80 Hz to 140 Hz, from 80 Hz to 130 Hz, from 80 Hz to 120 Hz, or from 80 Hz to 110 Hz. In an aspect, the frequency limits of partial power band 740 are from 200 Hz to 400 Hz. In one aspect, the frequency limits of partial power band 740 are from 105 Hz to 500 Hz, such as from 105 Hz to 400 Hz, from 105 Hz to 410 Hz, from 105 Hz to 420 Hz, from 105 Hz to 430 Hz, from 105 Hz to 440 Hz, from 105 Hz to 450 Hz, from 105 Hz to 460 Hz, from 105 Hz to 470 Hz, from 105 Hz to 480 Hz, from 105 Hz to 490 Hz, from 200 Hz to 500 Hz, from 200 Hz to 490 Hz, from 200 Hz to 480 Hz, from 200 Hz to 470 Hz, from 200 Hz to 460 Hz, from 200 Hz to 450 Hz, from 200 Hz to 440 Hz, from 200 Hz to 430 Hz, from 200 Hz to 420 Hz, or from 200 Hz to 410 Hz.

Figure 8A:
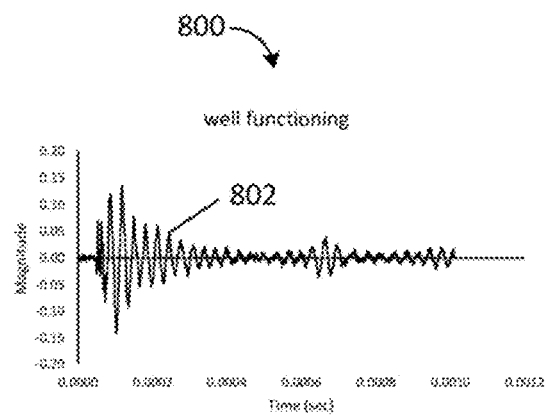
FIGS. 8A and 8B are plots of the signals from an acoustic sensor on two patients, in accordance with the present disclosure.
Figure 8B:
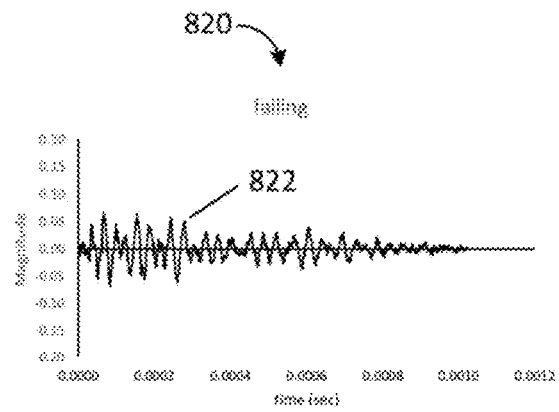

FIGS. 8A and 8B are plots 800, 820 of the signals 802, 822 from acoustic sensors on two patients, in accordance with the present disclosure. Signal 802 was received from an acoustic sensor proximate to a "well-functioning" implant while signal 822 was received from an acoustic sensor proximate to a "failing" implant. Signal 802 has a clear primary frequency, a waveform with a clear rise time and fall time, a lower-amplitude lower-frequency element that produces the increase in amplitude after time 0.0006, and very little higher-frequency noise. Signal 822, on the other hand, is lower in maximum amplitude than signal 802, does not have a clear single frequency, and does not show the clear rise time and fall time. At first glance, one might wrongly decide that the implant associated with signal 802 is more damaged than the implant associated with signal 822.

Figure 8C:
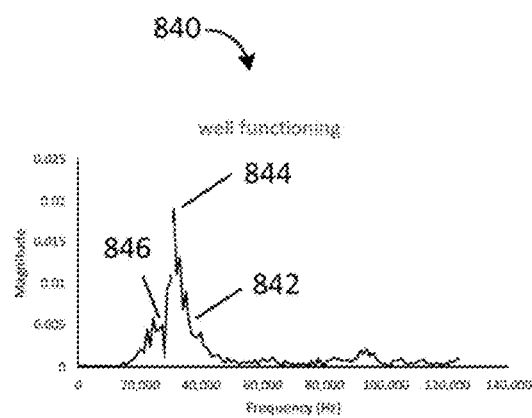
FIGS. 8C and 8D are plots of the Power Spectral Densities (PSDs) of the signals of FIGS. 8A and 8B, respectively, in accordance with the present disclosure.
Figure 8D:
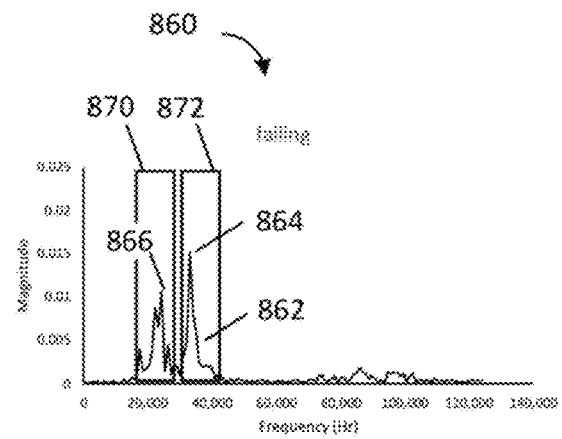

FIGS. 8C and 8D are plots 840, 860 of the PSDs 842, 862 of the signals 802, 822 of FIGS. 8A and 8B, respectively, in accordance with the present disclosure. PSD 842 has a first peak 846 and a second, larger peak 844. PSD 862 has a peak 866 at approximately the same frequency as peak 846 and a second, larger peak 864 at approximately the same frequency as peak 844. In an aspect, a ratio of the magnitude of peak 846 to the magnitude of peak 844 is calculated and compared to a ratio of the magnitude of peak 866 to the magnitude of peak 864. For example, the ratio of peaks 846, 844 is 0.27 while the ratio of peaks 866, 864 is 0.71, where the increase in the ratio is associated with a degradation in the implant associated with signal 822.

In an aspect, the specific frequencies of the peaks to be compared by ratio may vary slightly from person to person. In an aspect, the magnitude of the highest peak within a first frequency band, for example frequency band 870, may be compared to the magnitude of the highest peak within a second frequency band, for example frequency band 872. In an aspect, the ratio need not be a lower band over a higher band, e.g., either frequency band may define the numerator or denominator of a ratio. In an aspect, the partial powers within the frequency bands 870, 872 may be compared by ratio or difference.

From the foregoing, it will be appreciated that the present disclosure can be embodied in various ways, which include but are not limited to the following:

Embodiment 1

A method of identifying a loosened implant in a joint, the method comprising the steps of: positioning a plurality of acoustic sensors at a respective plurality of locations around the joint, causing the joint to be moved, receiving signals from the acoustic sensors during the movement of the joint, identifying signals from two or more of the plurality of acoustic sensors that correspond to a common acoustic event, identifying a position of the acoustic event within the joint, and providing a health indication related to the joint.

Embodiment 2

The method of embodiment 1, where the step of identifying a position comprises: calculating a first time delay between a first time of receipt of a first signal from a first acoustic sensor of the plurality of acoustic sensors and a second time of receipt of a second signal from a second acoustic sensor of the plurality of acoustic sensors, and calculating a first geometric surface of possible locations of the acoustic event from the first time delay.

Embodiment 3

The method of embodiment 2, where the step of identifying a position further comprises: calculating a second time delay between the first time of receipt and a third time of receipt of a third signal from a third acoustic sensor of the plurality of acoustic sensors, calculating a second geometric surface of possible locations of the acoustic event from the second time delay, and determining a line of intersection of the first and second geometric surfaces.

Embodiment 4

The method of embodiment 2, where the step of identifying a position further comprises determining where the first geometric surface intersects the implant.

Embodiment 5

The method of embodiment 2, where the step of calculating a first time delay comprises: identifying one or more types of tissue between the implant and the first acoustic sensor, identifying one or more signal paths from the implant to the first acoustic sensor, and adjusting the first time delay according to predetermined speeds of signal propagation within each of the one or more types of tissue and the signal paths.

Embodiment 6

The method of embodiment 1, where the step of identifying a position comprises: calculating a first magnitude difference between a first signal amplitude of a first signal from a first acoustic sensor of the plurality of acoustic sensors and a second signal magnitude of a second signal from a second acoustic sensor of the plurality of acoustic sensors, and calculating a first geometric surface of possible locations of the acoustic event from the first amplitude difference.

Embodiment 7

The method of embodiment 6, further comprising: adjusting the first time delay according to predetermined speeds of signal propagation within each of the one or more types of tissue and the signal paths.

Embodiment 8

A method of identifying a loosened implant in a joint, the method comprising the steps of: positioning an acoustic sensor at a location proximate to the joint, causing the joint to be moved, receiving a signal from the acoustic sensor during the movement of the joint, analyzing the signal to identify an attribute that is associated with a state of joint health, and providing a health indication related to the joint.

Embodiment 9

The method of embodiment 8, where the step of analyzing the signal comprises: calculating a rise time and a magnitude from the signal, comparing the rise time to a first threshold and the magnitude to a second threshold, and determining that the signal is indicative of a loose implant when the rise time exceeds the first threshold and the magnitude exceeds the second threshold.

Embodiment 10

The method of embodiment 8, where the step of analyzing the signal is performed only when the signal comprises a primary frequency within a predetermined band.

Embodiment 11

The method of embodiment 10, where the predetermined band is associated with the implant.

Embodiment 12

The method of embodiment 8, where the step of analyzing the signal comprises: calculating a power spectral density (PSD) of the signal, calculating a first partial power of the PSD within a predetermined first frequency band, comparing the first partial power to a first threshold, and determining that the signal is indicative of a loose implant when the first partial power exceeds the first threshold.

Embodiment 13

The method of embodiment 12, where the predetermined band includes a resonant frequency associated with the implant.

Embodiment 14

The method of embodiment 8, where the step of analyzing the signal comprises: calculating a power spectral density (PSD) of the signal, calculating a first partial power of the PSD within a predetermined first frequency band, calculating a second partial power of the PSD within a predetermined second frequency band, and comparing the first partial power to the second partial power.

Embodiment 15

The method of embodiment 14, where the step of comparing comprises: calculating a ratio of the first partial power to the second partial power, and determining that the signal is indicative of a loose implant when the ratio exceeds a threshold.

Embodiment 16

The method of embodiment 14, where the step of comparing comprises: calculating a difference between the first partial power and the second partial power, and determining that the signal is indicative of a loose implant is loose when the difference exceeds a threshold.

Embodiment 17

The method of embodiment 8, where the step of analyzing the signal comprises: calculating a power spectral density (PSD) of the signal, calculating a first maximum value of the PSD within a predetermined first frequency band, calculating a second maximum value of the PSD within a predetermined second frequency band, and comparing the first maximum value to the second maximum value.

Embodiment 18

The method of embodiment 8, where the step of providing a health indication related to the joint comprises: evaluating the total number of acoustic events indicative of a loose implant to determine a diagnostic indication of a loose implant.

Embodiment 19

An apparatus for identifying a loosened implant in a joint, the apparatus comprising the steps of: a plurality of acoustic sensors configured to be placed in contact with a patient's skin at a respective plurality of locations around the joint, a processor configured to receive signals from the acoustic sensors during the movement of the joint, where the processor is configured to: identify signals from two or more of the plurality of acoustic sensors that correspond to a common acoustic event, compare an attribute of the signals, identify a position of the acoustic event within the joint, and provide a health indication related to the joint.

While the present disclosure has been described with reference to particular aspects, it will be understood by those skilled in the art that various changes may be made and equivalents may be substituted for elements thereof without departing from the scope of the disclosure. In addition, many modifications may be made to a particular situation or material to the teachings of the disclosure without departing from the scope of the disclosure. Therefore, it is intended that the disclosure not be limited to the particular aspects disclosed but that the disclosure will include all aspects falling within the scope and spirit of the appended claims.

We claim:

1. An apparatus for identifying a loosened implant in a joint, the apparatus comprising:
    a plurality of acoustic sensors configured to be placed in contact with a patient's skin at a respective plurality of locations around the joint,
    a processor configured to receive signals from the acoustic sensors during the movement of the joint, and
    a non-transitory computer readable medium electronically coupled to the processor and comprising instructions stored thereon that when executed on the processor, perform the steps of:
        identifying signals from two or more of the plurality of acoustic sensors that correspond to a common acoustic event,
        comparing an attribute of the signals,
        identifying a position of the acoustic event within the joint, and
        providing a health indication related to the joint,
        wherein identifying a position comprises
            calculating a first time delay between a first time of receipt of a first signal from a first acoustic sensor of the plurality of acoustic sensors and a second time of receipt of a second signal from a second acoustic sensor of the plurality of acoustic sensors, and
            calculating a first geometric surface of possible locations of the acoustic event from the first time delay.

2. The apparatus of claim 1, wherein identifying a position of the acoustic event within the joint comprises
    calculating a second time delay between the first time of receipt and a third time of receipt of a third signal from a third acoustic sensor of the plurality of acoustic sensors,
    calculating a second geometric surface of possible locations of the acoustic event from the second time delay, and
    determining a line of intersection of the first and second geometric surfaces.

3. The apparatus of claim 1, wherein the non-transitory computer readable medium further comprises instructions that when executed on the processor, perform the step of determining where the first geometric surface intersects the implant.

4. The apparatus of claim 1, wherein calculating a first time delay comprises
    identifying one or more types of tissue between the implant and the first acoustic sensor;
    identifying one or more signal paths from the implant to the first acoustic sensor; and
    adjusting the first time delay according to predetermined speeds of signal propagation within each of the one or more types of tissue and the signal paths.

5. The apparatus of claim 1, wherein identifying a position of the acoustic event within the joint comprises
    calculating a first magnitude difference between a first signal amplitude of a first signal from a first acoustic sensor of the plurality of acoustic sensors and a second signal magnitude of a second signal from a second acoustic sensor of the plurality of acoustic sensors; and
    calculating a first geometric surface of possible locations of the acoustic event from the first amplitude difference.

6. The apparatus of claim 1, wherein calculating a first time delay comprises
    adjusting the first time delay according to predetermined speeds of signal propagation within each of the one or more types of tissue and the signal paths.

7. An apparatus for identifying a loosened implant in a joint, the apparatus comprising:
    an acoustic sensor configured to be placed in contact with a patient's skin at a location proximate to the joint,
    a processor configured to receive signals from the acoustic sensor during the movement of the joint, and
    a non-transitory computer readable medium electronically coupled to the processor and comprising instructions stored thereon that when executed on the processor, perform the steps of:
        analyzing the signal to identify an attribute that is associated with a state of joint health only when the signal comprises a primary frequency within a predetermined band, and
        providing a health indication related to the joint.

8. The apparatus of claim 7, wherein the predetermined band is associated with the implant.

9. An apparatus for identifying a loosened implant in a joint, the apparatus comprising:
    an acoustic sensor configured to be placed in contact with a patient's skin at a location proximate to the joint,
    a processor configured to receive signals from the acoustic sensor during the movement of the joint, and
    a non-transitory computer readable medium electronically coupled to the processor and comprising instructions stored thereon that when executed on the processor, perform the steps of:
        analyzing the signal to identify an attribute that is associated with a state of joint health only when the signal comprises a primary frequency within a predetermined band, and
        providing a health indication related to the joint,
        wherein analyzing the signal comprises calculating a power spectral density (PSD) of the signal, calculating a first partial power of the PSD within a predetermined first frequency band, comparing the first partial power to a first threshold, and determining that the signal is indicative of a loose implant when the first partial power exceeds the first threshold.

10. The apparatus of claim 9, wherein the predetermined band includes a resonant frequency associated with the implant.

11. An apparatus for identifying a loosened implant in a joint, the apparatus comprising:

an acoustic sensor configured to be placed in contact with a patient's skin at a location proximate to the joint, and a processor configured to receive signals from the acoustic sensor during the movement of the joint, and a non-transitory computer readable medium electronically coupled to the processor and comprising instructions stored thereon that when executed on the processor, perform the steps of:

analyzing the signal to identify an attribute that is associated with a state of joint health only when the signal comprises a primary frequency within a predetermined band, and providing a health indication related to the joint, wherein analyzing the signal comprises calculating a power spectral density (PSD) of the signal, calculating a first partial power of the PSD within a predetermined first frequency band, calculating a second partial power of the PSD within a predetermined second frequency band, comparing the first partial power to the second partial power.

12. The apparatus of claim 11, wherein comparing the first partial power to the second partial power comprises calculating a ratio of the first partial power to the second partial power, and determining that the signal is indicative of a loose implant when the ratio exceeds a threshold.

13. The apparatus of claim 11, wherein comparing the first partial power to the second partial power comprises calculating a difference between the first partial power and the second partial power, and determining that the signal is indicative of a loose implant is loose when the difference exceeds a threshold.

14. An apparatus for identifying a loosened implant in a joint, the apparatus comprising:

an acoustic sensor configured to be placed in contact with a patient's skin at a location proximate to the joint, and a processor configured to receive signals from the acoustic sensor during the movement of the joint, and a non-transitory computer readable medium electronically coupled to the processor and comprising instructions stored thereon that when executed on the processor, perform the steps of:

analyzing the signal to identify an attribute that is associated with a state of joint health, and providing a health indication related to the joint, wherein analyzing the signal comprises calculating a power spectral density (PSD) of the signal, calculating a first maximum value of the PSD within a predetermined first frequency band, calculating a second maximum value of the PSD within a predetermined second frequency band, and comparing the first maximum value to the second maximum value.

\* \* \* \* \*